United States Patent [19]
Audousset et al.

[11] Patent Number: 5,968,206
[45] Date of Patent: Oct. 19, 1999

[54] COMPOSITIONS AND PROCESSES FOR THE OXIDATIVE DYEING OF KERATIN FIBERS WITH PARA-PHENYLENEDIAMINE DERIVATIVES AND 4-HYDROXYINDULE AT BASIC PH'S

[75] Inventors: Marie-Pascale Audousset, Asnieres; Jean Cotteret, Verneuil sur Seine, both of France

[73] Assignee: L'Oreal, Paris, France

[21] Appl. No.: 09/107,136

[22] Filed: Jun. 30, 1998

Related U.S. Application Data

[63] Continuation of application No. 08/589,373, Jan. 22, 1996, abandoned.

[30] Foreign Application Priority Data

Jan. 20, 1995 [FR] France .................................. 95-00662

[51] Int. Cl.$^6$ ...................................................... A61K 7/13
[52] U.S. Cl. ........................... 8/409; 8/408; 8/410; 8/423
[58] Field of Search ............................... 8/406, 410, 409, 8/423, 408

[56] References Cited

U.S. PATENT DOCUMENTS

| | | | |
|---|---|---|---|
| 5,391,206 | 2/1995 | Cotteret | 8/408 |
| 5,540,738 | 7/1996 | Chan et al. | 8/406 |
| 5,609,649 | 3/1997 | Junino et al. | 8/409 |

FOREIGN PATENT DOCUMENTS

| | | |
|---|---|---|
| 0 428 441 | 5/1991 | European Pat. Off. . |
| 0 465 340 | 1/1992 | European Pat. Off. . |
| 3031709 | 4/1982 | Germany . |
| 3743769 | 7/1989 | Germany . |
| 3942294 | 6/1991 | Germany . |

OTHER PUBLICATIONS

ASTM Designation: D1535–95b, "Standard Practice for Specifying Color by the Munsell System," pp. 1–3 (1995).

*Primary Examiner*—Caroline D. Liott
*Attorney, Agent, or Firm*—Finnegan, Henderson, Farabow, Garrett & Dunner, L.L.P.

[57] ABSTRACT

A ready-to-use composition for the oxidation dyeing of keratinous fibers, especially of human keratinous fibers such as hair, which comprises, in an alkaline medium (pH>7), an appropriately selected para-phenylenediamine derivative in combination with 4-hydroxyindole and an oxidizing agent, and dyeing processes using this composition.

17 Claims, No Drawings

COMPOSITIONS AND PROCESSES FOR THE OXIDATIVE DYEING OF KERATIN FIBERS WITH PARA-PHENYLENEDIAMINE DERIVATIVES AND 4-HYDROXYINDULE AT BASIC PH'S

This is a continuation of application Ser. No. 08/589,373, filed Jan. 22, 1996, which is incorporated herein by reference, now abandoned.

The present invention relates to a ready-to-use composition for the oxidation dyeing of keratinous fibers, especially of human keratinous fibers such as hair, which comprises, in an alkaline medium, an appropriately selected para-phenylenediamine derivative in combination with 4-hydroxyindole and an oxidizing agent, and to the dyeing process using this composition. It also relates to a dyeing kit which can be used for the preparation of such a composition.

It is known to dye keratinous fibers, and especially human hair, with dyeing compositions containing oxidation dye precursors, in particular ortho- or para-phenylenediamines or ortho- or para-aminophenols, which are generally referred to as oxidation bases. Oxidation dye precursors, or oxidation bases, are colourless or slightly coloured compounds which, combined with oxidizing products, are able by a process of oxidative condensation to give rise to coloured compounds and dyes.

It is also known that it is possible to vary the shades obtained with these oxidation bases by combining them with couplers or dye modifiers, the latter being chosen in particular from aromatic meta-diamines, meta-aminophenols and meta-diphenols and certain indole compounds such as 4-hydroxyindole.

The variety of the molecules employed as oxidation bases and as couplers makes it possible to obtain a rich palette of colours.

The so-called permanent coloration which is obtained by virtue of these oxidation dyes must, moreover, satisfy a certain number of demands. Thus it must be without disadvantage from the toxicological standpoint, it should enable shades of the desired intensity to be obtained, and it must be of good persistence vis-à-vis external agents (light, inclement weather, washing, perming, perspiration, rubbing).

The dyes must also make it possible to cover white hair, and finally they should be as unselective as possible; in other words, they should make it possible to obtain minimal deviations in coloration right along a single keratinous fiber, which can in fact be of differing sensitivity (i.e. damaged) between its end and its root.

Proposals have already been made, in particular in German Patent Application DE 3 031 709, for compositions for the oxidation dyeing of keratinous fibers which comprise an oxidation base, such as para-phenylenediamine or para-aminophenol, and 4-hydroxyindole as coupler. However, such compositions are not entirely satisfactory, especially with regard to the persistence of the resulting colorations vis-à-vis external agents, and in particular vis-à-vis shampooing.

There have also already been proposals, in particular in French Patent Application FR 2 664 304, for compositions for the oxidation dyeing at an acid pH of keratinous fibers, which compositions comprise at least one oxidation dye precursor and 4-hydroxyindole as coupler. However, such compositions are also not entirely satisfactory, in particular with regard to the selectivity of the colorations obtained.

The Applicant has recently discovered that it is possible to obtain novel dyes which give rise to intense colorations, less selective than the prior art colorations, and which are obtained at an acid pH and are more resistant, especially to shampooing, than the prior art colorations obtained at an alkaline pH, by combining:

at least one appropriately selected para-phenylenediamine derivative as defined below as oxidation base,
4-hydroxyindole as coupler,
at least one oxidizing agent,
the pH of the resulting dyeing composition being greater than or equal to 7.

It is this discovery which forms the basis of the present invention.

The subject of the invention is therefore a ready-to-use composition for the oxidation dyeing of keratinous fibers, and especially of human keratinous fibers such as hair, which is characterized in that it comprises, in a medium appropriate for dyeing:

at least one oxidation base chosen from para-phenylenediamine derivatives of formulae (I) and (II) below:

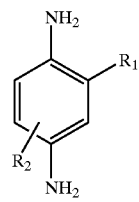

(I)

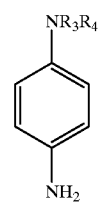

(II)

in which:
$R_1$ represents a $C_1$–$C_4$ alkyl or $C_2$–$C_4$ monohydroxyalkoxy radical;
$R_2$ represents a hydrogen atom or a $C_1$–$C_4$ alkyl radical; with the proviso (i) that, if $R_2$ represents a $C_1$–$C_4$ alkyl radical, $R_1$ is identical to $R_2$, and (ii) that, if $R_1$ is in the meta position relative to $R_2$, $R_1$, and $R_2$ cannot simultaneously designate an ethyl radical, and (iii) that, if $R_1$ is in the ortho position relative to $R_2$, $R_1$ and $R_2$ cannot simultaneously designate a methyl radical, and (iv) that, if $R_2$ denotes a hydrogen atom, $R_1$ cannot denote a methyl radical;
$R_3$ represents a hydrogen atom or a $C_1$–$C_4$ monohydroxyalkyl or $C_2$–$C_4$ polyhydroxyalkyl radical;
$R_4$ represents a $C_1$–$C_4$ monohydroxyalkyl, $C_2$–$C_4$ polyhydroxyalkyl or $C_1$–$C_4$ alkoxyalkyl radical,
with the proviso that, if $R_4$ represents a $C_1$–$C_4$ alkoxyalkyl radical, $R_3$ represents a hydrogen atom,
and their addition salts with an acid,
4-hydroxyindole as coupler,
at least one oxidizing agent,
the pH of this ready-to-use composition being greater than or equal to 7.

The colorations obtained with dyeing compositions according to the invention are less selective than those of the prior art and, moreover, are of good dyeing strength and have excellent properties or resistance both to atmospheric agents, such as light and inclement weather, and to perspiration and the various treatments to which hair may be subject (washing, perming).

Another subject of the invention is a process for the oxidation dyeing of keratinous fibers using this dyeing composition.

The addition salts with an acid which can be used within the scope of the dyeing compositions of the invention are in particular chosen from hydrochlorides, hydrobromides, sulphates and tartrates.

Among the para-phenylenediamine derivatives of formulae (I) and (II) above, more particular mention may be made of 2,6-dimethyl-para-phenylenediamine, 2,5-dimethyl-para-phenylenediamine, 1-N-(β-methoxyethyl) amino-4-aminobenzene, 2-β-hydroxyethyloxy-para-phenylenediamine and N, N'-bis(β-hydroxyethyl)amino-4-aminobenzene, and their addition salts with an acid.

The para-phenylenediamine derivative or derivatives preferably represent from approximately 0.0005 to 10% by weight of the total weight of the dyeing composition, and still more preferably from approximately 0.01 to 5% by weight.

The 4-hydroxyindole preferably represents from approximately 0.0001 to 3.5% by weight of the total weight of the dyeing composition, and still more preferably from approximately 0.005 to 1% by weight.

The pH of the dyeing composition as defined above can vary from 7 to 12, and preferably from 8 to 11, and can be adjusted to the desired value by means of acidifying or basifying agents which are customarily used in the dyeing of keratinous fibers.

Among the acidifying agents mention may be made by way of example of mineral acids or organic acids, such as hydrochloric acid, orthophosphoric acid, carboxylic acids such as tartaric acid, citric acid and lactic acid, and sulphonic acids.

Among the basifying agents mention may be made by way of example of aqueous ammonia, alkali metal carbonates, alkanolamines such as mono-, di- and triethanolamines, and derivatives thereof, sodium hydroxide or potassium hydroxide, and the compounds of formula (III) below:

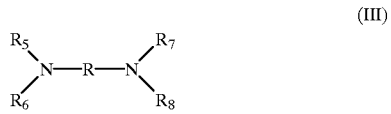

(III)

in which R is a propylene radical which is optionally substituted with a hydroxyl group or a $C_1$–$C_4$ alkyl radical; $R_5$, $R_6$, $R_7$ and $R_8$, which are identical or different, represent a hydrogen atom or a $C_1$–$C_4$ alkyl or $C_1$–$C_4$ hydroxyalkyl radical.

The oxidizing agent which is present in the dyeing composition is chosen from the oxidizing agents which are conventionally used in oxidation dyeing, and preferably from hydrogen peroxide, urea peroxide, alkali metal bromates, and persalts such as perborates and persulphates. Hydrogen peroxide is particularly preferred.

The dyeing composition according to the invention can also contain, in addition to the dyes defined above, other couplers and/or direct dyes, in particular for modifying the shades or enriching them with glints.

The medium appropriate for dyeing (or vehicle) of the dyeing compositions consists in general of water or of a mixture of water and at least one organic solvent in order to solubilize the compounds which would not be sufficiently soluble in water. As organic solvent mention may be made for example of $C_1$–$C_4$ lower alkanols, such as ethanol and isopropanol; glycerol, glycols and glycol ethers, such as 2-butoxyethanol, propylene glycol, propylene glycol monomethyl ether, diethylene glycol monoethyl ether and monomethyl ether, and aromatic alcohols, such as benzyl alcohol or phenoxyethanol, similar products and mixtures thereof.

The solvents can be present in proportions which are preferably from approximately 1 to 40% by weight relative to the total weight of the dyeing composition, and still more preferably from approximately 5 to 30% by weight.

The dyeing compositions according to the invention can also contain various adjuvants which are conventionally used in hair-dyeing compositions, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersants, conditioners, film-formers, preservatives and opacifying agents.

The dyeing compositions according to the invention can be presented in various forms, such as in the form of liquids, creams or gels, or in any other form which is appropriate for dyeing keratinous fibers, and especially human hair.

Another subject of the invention is a process for dyeing keratinous fibers, and especially human keratinous fibers such as hair, using the dyeing composition as defined above.

In accordance with this process, the dyeing composition as defined above is applied to the fibers and allowed to act for from approximately 3 to 40 minutes, preferably from approximately 5 to 30 minutes, after which the fibers are rinsed, washed optionally with shampoo, rinsed again and dried.

In accordance with a preferred embodiment, the process includes a preliminary step which consists in storing, separately, on the one hand a composition (A) comprising, in a medium appropriate for dyeing, at least one para-phenylenediamine derivative according to the invention and 4-hydroxyindole and, on the other hand, a composition (B) comprising, in a medium appropriate for dyeing, at least one oxidizing agent as defined above, and in mixing these components at the time of use before applying this mixture to the keratinous fibers, the pH of compositions (A) and (B) being such that, after mixing from 10 to 90% of the composition (A) with from 90 to 10% of the composition (B), the pH of the resulting mixture is greater than or equal to 7.

The pH of the compositions (A) and (B) can be adjusted to the desired value by means of conventional basifying or acidifying agents such as those defined above.

Yet another subject of the invention is a multi-compartment device or dyeing kit or any other packaging system comprising a plurality of compartments, of which a first compartment contains the composition (A) as defined above and a second compartment contains the oxidizing composition (B) as defined above. These devices can be equipped with a means making it possible to supply the desired mixture to the hair, such as the devices described in the Applicant's patent FR-2 586 913.

The examples which follow are intended to illustrate the invention without, however, limiting its scope.

EXAMPLES

Examples 1 and 2

The following compositions 1(A) and 2(A), in accordance with the invention, were prepared (contents in grams):

| COMPOSITION | 1(A) | 2(A) |
|---|---|---|
| 2,6-Dimethyl-para-phenylenediamine dihydrochloride | 0.4 | |
| N,N'-Bis(β-hydroxyethyl)amino-4-aminobenzene sulphate | | 0.3 |
| 4-Hydroxyindole | 0.6 | 0.3 |
| Common dye vehicle (*) | (*) | (*) |
| Water qs | 100 g | 100 g |

(*) common dye vehicle:

| | |
|---|---|
| - Oleyl alcohol, polyglycerolated with 2 mol of glycerol | 4.0 g |
| - Oleyl alcohol, polyglycerolated with 4 mol of glycerol, containing 78% of active substances (AS) | 5.69 g AS |
| - Oleic acid | 3.0 g |
| - Oleylamine with 2 mol of ethylene oxide, sold under the tradename ETHOMEEN O12 by the company AKZO | 7.0 g |
| - Diethylaminopropyl laurylaminosuccinamate, sodium salt, containing 55% AS | 3.0 g AS |
| - Oleyl alcohol | 5.0 g |
| - Oleic acid diethanolamide | 12.0 g |
| - Propylene glycol | 3.5 g |
| - Ethyl alcohol | 7.0 g |
| - Dipropylene glycol | 0.5 g |
| - Propylene glycol monomethyl ether | 9.0 g |
| - Sodium metabisulphite in aqueous solution containing 35% of AS | 0.455 g AS |
| - Ammonium acetate | 0.8 g |
| - Antioxidant, sequestering agent | qs |
| - Fragrance, preservative | qs |
| - Aqueous ammonia containing 20% NH$_3$ | 10.0 g |

At the time of use, each composition 1(A) and 2(A) was mixed with an equal quantity of a composition (B) consisting of 20-volume hydrogen peroxide solution (6% by weight).

Each resulting composition (ready-to-use composition in accordance with the invention, of pH≧7) was applied for 30 minutes to locks of grey hair containing 90% white hairs, which were either natural or permed. The locks of hair were subsequently rinsed, washed with a standard shampoo and then dried.

The locks of hair were dyed in the shades indicated in the table below:

| EXAMPLE [COMPOSITION] | SHADE ON NATURAL HAIR | SHADE ON PERMED HAIR |
|---|---|---|
| 1 [1(A)] | purplish-blue ash | strong purplish-blue ash |
| 2 [2(A)] | light ash blue | intense blue |

Comparative Examples 3 and 4

The following compositions 3(A) and 4(A) were prepared:

Composition 3(A), not part of the invention:

| | |
|---|---|
| - Para-phenylenediamine (4 × 10$^{-3}$ mol) | 0.432 g |
| - 4-hydroxyindole | 0.532 g |
| - Common dye vehicle defined in Examples 1 and 2 | (*) g |
| - Water qs | 100 g |

Composition 4(A) in accordance with the invention:

| | |
|---|---|
| - 2,6-dimethyl-para-phenylenediamine dihydrochloride (4 × 10$^{-3}$ mol) | 0.836 g |
| - 4-hydroxyindole | 0.532 g |
| - Common dye vehicle defined in Examples 1 and 2 | (*) g |
| - Water qs | 100 g |

At the time of use, each composition 3(A) and 4(A) was mixed with an equal quantity of a composition (B) consisting of 20-volume hydrogen peroxide solution (6% by weight).

Each resulting composition had a pH≧7 and was applied for 30 minutes to locks of natural grey hair containing 90% white hairs. The locks of hair were subsequently rinsed, washed with a standard shampoo and then dried.

The colour of the locks was subsequently evaluated in the MUNSELL system by means of a MINOLTA CM 2002 colorimeter.

The locks of hair thus dyed were subsequently subjected to a shampooing-resistance test (Ahiba-Texomat machine):

The locks of hair were placed in a basket which was immersed in a solution of a standard shampoo at 37° C. The basket was subjected to an up-and-down movement of variable frequency and to a rotational movement, which movements reproduce the action of manual rubbing, leading to the formation of foam.

After 3 minutes of testing, the locks were withdrawn, rinsed and then dried. The dyed locks were subjected to 3 consecutive shampooing tests.

The colour of the locks was subsequently evaluated again in the MUNSELL system using a MINOLTA CM 2002 colorimeter in order to determine the deterioration in the colorations after these 3 shampooing operations.

According to the MUNSELL notation, a colour is defined by the expression HV/C in which the three parameters designate respectively the shade or hue (H), the intensity or value (V) and the purity or chromaticity (C), the oblique bar in this expression being simply a convention and not indicating a ratio.

The difference in colour between two locks is calculated by applying the formula of NICKERSON: $\Delta E = 0.4\ Co\Delta H + 6\Delta V + 3\ \Delta C$, as is described for example in "Couleur, Industrie et Technique"; pages 14–17; vol. No. 5; 1978.

In this formula, $\Delta E$ represents the difference in colour between two locks, $\Delta H$, $\Delta V$ and $\Delta C$ represent the variation in the absolute value of the parameters H, V and C, and Co represents the purity of the lock relative to which the difference in colour is to be evaluated.

The results are given in the table below:

| EXAMPLE [COMPOSITION] | Hair colour before shampooing | Hair colour after shampooing | Deterioration in colour | | | |
|---|---|---|---|---|---|---|
| | | | $\Delta H$ | $\Delta V$ | $\Delta C$ | $\Delta E$ |
| 3 [3(A)] | 7.4 P 2.3/1.8 | 8.7 P 2.3/1.5 | 1.3 | 0 | 0.3 | 1.84 |
| 4 [4(A)] | 2.2 P 2.8/1.7 | 2.2 P 2.8/1.6 | 0 | 0 | 0.1 | 0.3 |

These results show that the composition of Example 4 in accordance with the invention leads to a coloration which is more resistant to shampooing than the composition of Example 3, as is described for example in the German Patent Application DE 3 031 709, and which is not part of the invention.

Comparative Examples 5 and 6

The following compositions 5(A) and 6(A) were prepared:

Composition 5(A):

| | |
|---|---|
| - 2,6-Dimethyl-para-phenylenediamine dihydrochloride | 0.4 g |
| - 4-Hydroxyindole | 0.6 g |
| - Common dye support defined in Examples 1 and 2 | (*) g |
| - Water qs | 100 g |

Composition 6(A):

| | |
|---|---|
| - 2,6-Dimethyl-para-phenylenediamine dihydrochloride | 0.4 g |
| - 4-Hydroxyindole | 0.6 g |
| - Common dye support defined in Examples 1 and 2 but in which the aqueous ammonia has been replaced by a quantity of monoethanolamine sufficient to adjust the pH to 9.8 | (*) g |
| - Water qs | 100 g |

Dyeing process for Example 5 in accordance with the invention:

At the time of use, the composition 5(A) was mixed with an equal quantity of a composition 5(B) consisting of 20-volume hydrogen peroxide solution (6% by weight).

The resulting composition, having a pH of 9.8, was applied for 30 minutes on the one hand to locks of natural grey hair containing 90% white hairs (lock of nonsensitized hair no. 1) and on the other hand to a lock of the same grey hair containing 90% white hairs but which has undergone permanent waving (lock of sensitized hair no. 2). The locks of hair were subsequently rinsed, washed with a standard shampoo and then dried.

The colour of the locks was subsequently evaluated in the MUNSELL system using a MINOLTA CM 2002 colorimeter.

The difference in colour between natural hair (nonsensitized) and permed hair (sensitized) was calculated by applying the NICKERSON formula.

Dyeing process for Example 6, not part of the invention:

At the time of use, the composition 6(A) was mixed with an equal quantity of a composition 6(B) consisting of 20-volume hydrogen peroxide solution (6% by weight) whose pH was adjusted to between 1 and 1.5 with 2.5 g of orthophosphoric acid per 100 g of hydrogen peroxide.

The resulting composition, having a pH of 6.8, was applied for 30 minutes on the one hand to locks of natural grey hair containing 90% white hairs (lock of nonsensitized hair no. 1) and on the other hand to a lock of the same grey hair containing 90% white hairs but having undergone permanent waving (lock of sensitized hair no. 2). The locks of hair were subsequently rinsed, washed with a standard shampoo and then dried.

The colour of the locks was subsequently evaluated in the MUNSELL system using a MINOLTA CM 2002 colorimeter.

The difference in colour between natural hair (nonsensitized) and permed hair (sensitized) was calculated by applying the NICKERSON formula.

The selectivity results for Examples 5 and 6 are given in the table below:

| EXAMPLE [COMPOSITION] | Colour on natural hair | Colour on permed hair | Difference in colour (selectivity) | | | |
|---|---|---|---|---|---|---|
| | | | ΔH | ΔV | ΔC | ΔE |
| 5 [5(A)] | 2.9 P 2.1/2.5 | 8.7 PB 0.1/5.0 | 4.2 | 2.0 | 2.5 | 23.7 |
| 6 [6(A)] | 9.5 PB 1.2/4.5 | 0.2 PB 0/2.4 | 9.3 | 1.2 | 2.1 | 30.24 |

These results show that the coloration obtained at an alkaline pH by the process according to the invention is less selective than the coloration obtained at an acid pH by the prior art process as described, for example, in French Patent Application FR 2 664 304.

What is claimed is:

1. A composition for the oxidation dyeing of keratinous fibers comprising, in a medium appropriate for dyeing:

(a) at least one oxidation base of para-phenylenediamine derivatives of formulae (I) or (II) below:

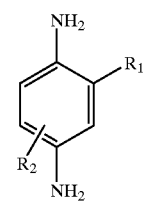

(I)

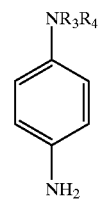

(II)

in which:

$R_1$ represents a $C_1$–$C_4$ alkyl or $C_2$–$C_4$ monohydroxyalkoxy radical;

$R_2$ represents a hydrogen atom or a $C_1$–$C_4$ alkyl radical; with the proviso (I) that, if $R_2$ represents a $C_1$–$C_4$ alkyl radical, $R_1$ is identical to $R_2$, and (ii) that, if $R_1$ is in the meta position relative to $R_2$, $R_1$ and $R_2$ cannot simultaneously designate an ethyl radical, and (iii) that, if $R_1$ is in the ortho position relative to $R_2$, $R_1$ and $R_2$ cannot simultaneously designate a methyl radical, and (iv) that, if $R_2$ denotes a hydrogen atom, $R_1$ cannot denote a methyl radical;

$R_3$ represents a hydrogen atom, a $C_1$–$C_4$ monohydroxyalkyl, or a $C_2$–$C_4$ polyhydroxyalkyl radical;

$R_4$ represents a $C_1$–$C_4$ monohydroxyalkyl, $C_2$–$C_4$ polyhydroxyalkyl or $C_1$–$C_4$ alkoxyalkyl radical, with the proviso that, if $R_4$ represents a $C_1$–$C_4$ alkoxyalkyl radical, $R_3$ represents a hydrogen atom, or their addition salts with an acid;

(b) 4-hydroxyindole as coupler; and (c) at least one oxidizing agent, wherein the pH of the composition is greater than 7; and further wherein said at least one oxidation base, said coupler and said at least one oxidizing agent are present in an amount effective to dye said keratinous fibers.

2. A composition according to claim 1, wherein the keratinous fibers are human hair.

3. A composition according to claim 1, wherein the addition salts with an acid are hydrochlorides, hydrobromides, sulphates, or tartrates.

4. A composition according to claim 1, wherein the para-phenylenediamine derivatives of formulae (I) and (II) are 2,6-dimethyl-para-phenylenediamine, 2,5-dimethyl-para-phenylenediamine, 1-N-(β-methoxyethyl) amino-4-aminobenzene, 2-β-hydroxyethyloxy-para-phenylenediamine or N,N'-bis(β-hydroxyethyl)amino-4-aminobenzene, or their addition salts with an acid.

5. A composition according to claim 1, wherein the para-phenylenediamine derivative is present in an amount ranging from about 0.0005 to 10% by weight of the total weight of the dyeing composition.

6. A composition according to claim 5, wherein the para-phenylenediamine derivative is present in an amount ranging from about 0.01 to 5% by weight of the total weight of the dyeing composition.

7. A composition according to claim 1, wherein the 4-hydroxyindole is present in an amount ranging from about 0.0001 to 3.5% by weight of the total weight of the dyeing composition.

8. A composition according to claim 7, wherein the 4-hydroxyindole is present in an amount ranging from about 0.005 to 1% by weight of the total weight of the dyeing composition.

9. A composition according to claim 1, wherein the composition has a pH ranging from greater than 7 to 12.

10. A composition according to claim 9, wherein the composition has a pH ranging from about 8 to 11.

11. A composition according to claim 1, wherein the oxidizing agent is hydrogen peroxide, urea peroxide, alkali metal bromate, or persalt.

12. A composition according to claim 11, wherein the persalt is perborate or persulphate.

13. A composition according to claim 1, wherein the composition additionally comprises at least one adjuvant selected from anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersants, conditioners, film-formers, preservatives or opacifying agents.

14. A composition according to claim 1, wherein the composition is in the form of a liquid, a cream or a gel, or in any other form which is appropriate for dyeing keratinous fibers.

15. A process for dyeing keratinous fibers, comprising the step of applying the dyeing composition as claimed in claim 1 to the fibers.

16. A process for dyeing keratinous fibers, comprising the steps of separately storing a composition (A) from a composition (B), wherein composition (A) comprises, in a medium appropriate for dyeing, 4-hydroxyindole and at least one para-phenylenediamine derivative selected from formulae (I) or (II) below:

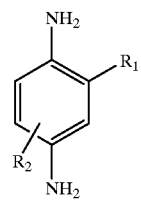

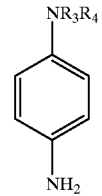

in which:

$R_1$ represents a $C_1$–$C_4$ alkyl or $C_2$–$C_4$ monohydroxyalkoxy radical;

$R_2$ represents a hydrogen atom or a $C_1$–$C_4$ alkyl radical;

with the proviso (i) that, if $R_2$ represents a $C_1$–$C_4$ alkyl radical, $R_1$ is identical to $R_2$, and (ii) that, if $R_1$ is in the meta position relative to $R_2$, $R_1$ and $R_2$ cannot simultaneously designate an ethyl radical, and (iii) that, if $R_1$ is in the ortho position relative to $R_2$, $R_1$ and $R_2$ cannot simultaneously designate a methyl radical, and (iv) that, if $R_2$ denotes a hydrogen atom, $R_1$ cannot denote a methyl radical;

$R_3$ represents a hydrogen atom, a $C_1$–$C_4$ monohydroxyalkyl, or a $C_2$–$C_4$ polyhydroxyalkyl radical;

$R_4$ represents a $C_1$–$C_4$ monohydroxyalkyl, $C_2$–$C_4$ polyhydroxyalkyl or $C_1$–$C_4$ alkoxyalkyl radical, with the proviso that, if $R_4$ represents a $C_1$–$C_4$ alkoxyalkyl radical, $R_3$ represents a hydrogen atom, or their addition salts with an acid, and wherein composition (B) comprises, in a medium appropriate for dyeing, at least one oxidizing agent selected from hydrogen peroxide, urea peroxide, alkali metal bromate, or persalt, mixing said compositions (A) and (B) at the time of application, and applying the mixture to the keratinous fibers, the pH of compositions (A) and (B) being such that, after mixing from 10 to 90% of the composition (A) with from 90 to 10% of the composition (B), the pH of the resulting mixture is greater than 7.

17. A multi-compartment kit for dyeing, comprising a first compartment containing a composition (A), wherein said composition (A) comprises, in a medium appropriate for dyeing, 4-hydroxyindole and at least one para-phenylenediamine derivative selected from formulae (I) or (II) below;

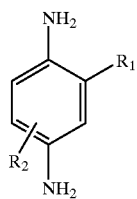
(I)

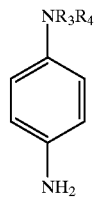
(II)

in which:
- $R_1$ represents a $C_1$–$C_4$ alkyl or $C_2$–$C_4$ monohydroxyalkoxy radical:
- $R_2$ represents hydrogen atom or a $C_1$–$C_1$ alkyl radical; with the proviso (i) that, if $R_2$ represents a $C_1$–$C_4$ alkyl radical, $R_1$ is identical to $R_2$, and (ii) that, if $R_1$ is in the meta position relative to $R_2$, $R_2$ and $R_2$ cannot simultaneously designate an ethyl radical, and (iii) that, if $R_1$ is in the ortho position relative to $R_2$, $R_1$ and $R_2$ cannot simultaneously designate a methyl radical, and (iv) that, if $R_2$ denotes a hydroden atom, $R_1$ cannot designate a methyl radical;
- $R_3$ represents hydrogen atom, a $C_1$–$C_4$ monohydroxyalkyl, or a $C_2$–$C_4$ potyhydroxyalkyl radical;
- $R_4$ represents a $C_1$–$C_4$ monohydroxyalkyl, $C_2$–$C_4$ polyhydroxyalkyl or $C_1$–$C_4$ alkoxyalkyl radical, with the proviso that, if $R_4$ represents a $C_1$–$C_4$ alkoxyalkyl radical, $R_3$ represents a hydrogen atom, or their addition salts with an acid; and a second compartment containing a composition (B), wherein said composition (B) comprises, in a medium appropriate for dyeing, at least one oxidizing agent selected from hydrogen peroxide, urea Peroxide, alkali metal bromate, or per-salt;

the pH of the compositions (A) and (B) being such that, after mixing from 10 to 90% of the compositions (A) with 90to10% of the composition (B), the pH of the resulting mixture is greater than 7.

* * * * *

UNITED STATES PATENT AND TRADEMARK OFFICE
CERTIFICATE OF CORRECTION

PATENT NO.: 5,968,206
DATED: October 19, 1999
INVENTOR(S): Marie-Pascale AUDOUSSET et al.

It is certified that an error appears in the above-identified patent and that said Letters Patent is hereby corrected as shown below:

On the title page, item [54] and column 1:

Line 4, change "4-HYDROXYINDULE" to --4-HYDROXYINDOLE--.

IN THE CLAIMS:

Claim 17, col. 11, line 22, change "monohydroxyla" to --monohydroxyl--;

line 23, change "lkoxy" to --alkoxy--;

col. 12, line 1, change "$R_2$" (second occurrence) to --$R_1$--;

line 3, change "$R_1$is" to --$R_1$ is--;

line 5, change "hydroden" to --hydrogen--;

line 8, change "potyhydroxyalkyl" to --polyhydroxyalkyl--;

line 19, change "Peroxide" (second occurrence) to --peroxide--; and line 23, change "90to10%" to --from 90 to 10%--.

Signed and Sealed this

Eighteenth Day of April, 2000

*Attest:*

Q. TODD DICKINSON

*Attesting Officer*   *Director of Patents and Trademarks*